(12) United States Patent
Minowa et al.

(10) Patent No.: US 7,795,464 B2
(45) Date of Patent: Sep. 14, 2010

(54) METHOD FOR PRODUCING α-AMINO ACID INCLUDING PHOSPHORUS AND PRODUCTION INTERMEDIATES THEREOF

(75) Inventors: Nobuto Minowa, Kanagawa (JP); Nozomu Nakanishi, Kanagawa (JP); Masaaki Mitomi, Kanagawa (JP)

(73) Assignee: Meiji Seika Kaisha Ltd., Tokyo (JP)

( * ) Notice: Subject to any disclaimer, the term of this patent is extended or adjusted under 35 U.S.C. 154(b) by 26 days.

(21) Appl. No.: 12/442,011

(22) PCT Filed: Sep. 19, 2007

(86) PCT No.: PCT/JP2007/068115
§ 371 (c)(1),
(2), (4) Date: Mar. 19, 2009

(87) PCT Pub. No.: WO2008/035687
PCT Pub. Date: Mar. 27, 2008

(65) Prior Publication Data
US 2009/0270647 A1    Oct. 29, 2009

(30) Foreign Application Priority Data
Sep. 20, 2006    (JP) .............................. 2006-254102

(51) Int. Cl.
*C07F 9/32* (2006.01)
(52) U.S. Cl. .......................... 558/145; 558/87
(58) Field of Classification Search ............... 558/145, 558/87
See application file for complete search history.

(56) References Cited

U.S. PATENT DOCUMENTS

| | | | |
|---|---|---|---|
| 4,168,963 | A | 9/1979 | Rupp et al. |
| 4,499,027 | A | 2/1985 | Minowa et al. |
| 4,692,541 | A | 9/1987 | Zeiss et al. |
| 4,777,279 | A | 10/1988 | Zeiss |
| 4,922,006 | A | 5/1990 | Zeiss |
| 5,051,525 | A | 9/1991 | Willms |
| 5,756,800 | A | 5/1998 | Willms et al. |
| 6,359,162 | B1 | 3/2002 | Willms |
| 6,686,181 | B1 | 2/2004 | Bartsch |
| 6,936,444 | B1 | 8/2005 | Bartsch |

FOREIGN PATENT DOCUMENTS

| | | |
|---|---|---|
| JP | 52-139727 | 11/1977 |
| JP | 55-000025 | 1/1980 |
| JP | 59-219297 | 12/1984 |
| JP | 61-207398 A | 9/1986 |
| JP | 62-132891 | 6/1987 |
| JP | 62-226993 | 10/1987 |
| JP | 2-240089 A | 9/1990 |
| JP | 2-245197 A | 9/1990 |
| JP | 2003-505031 | 2/2003 |
| JP | 2003-528572 | 9/2003 |
| WO | 99/09039 A1 | 2/1999 |

OTHER PUBLICATIONS

Razumov et al., "Synthesis and Properties of Phosphorylated Imines and Enamines" *Zhurnal Obshchei Khimii* vol. 43, No. 5, pp. 1019-1026, 1973.
Murielle Chavarot et al., "Sc(BINOL)₂Li: A New Heterobimetallic Catalyst for the Asymmetric Strecker Reaction" *Tetrahedron: Asymmetry* vol. 12, pp. 1147-1150, 2001.
E. J. Corey et al., "Enantioselective Synthesis of α-Amino Nitriles from N-Benzhydryl Imines and HCN with a Chiral Bicyclic Guanidine as Catalyst" *Org. Lett.* vol. 1, No. 1, pp. 157-160, 1999.
Ewa Gruszecka et al., "Preparation of $_{D,L}$-Phosphinothricin by Strecker Reaction" *Polish Journal of Chemistry* vol. 53, pp. 937-939, 1979.
Ewa Gruszecka et al., "New Synthesis of Phosphinothricin and Analogues" *Roczniki Chemii Ann. Soc. Chim. Polonorum* vol. 49, pp. 2127-2128, 1975.
M. A. Smitha et al., "Photoinduced Electron Transfer in Hydrogen Bonded Donor—Acceptor Systems. Free Energy and Distance Dependence Struies and an Analysis of the Role of Diffusion" *J. Am. Chem. Soc.* vol. 123, pp. 1159-1165, 2001.
Haruro Ishitani et al., "Catalytic Asymmetric Strecker Synthesis. Preparation of Enantiomerically Pure α-Amino Acid Derivatives from Aldimines and Tributyltin Cyanide or Achiral Aldehydes, Amines, and Hydrogen Cyanide Using a Chiral Zirconium Catalyst" *J. Am. Chem. Soc.* vol. 122, pp. 762-766, 2000.
Matthew Sigman et al., "Enantioselective Addition of Hydrogen Cyanide to Imines Catalyzed by a Chiral (Salen)A1(III) Complex" *J. Am. Chem. Soc.* vol. 120, pp. 5315-5316, 1998.
Matthew Sigman et al., "Schiff Base Catalysts for the Asymmetric Strecker Reaction Identified and Optimized from Parallel Synthetic Libraries" *J. Am. Chem. Soc.* vol. 120, pp. 4901-4902, 1998.
Masahiro Takamura et al., "A Catalytic Asymmetric Strecker-Type Reaction: Interesting Reactivity Difference between TMSCN and HCN" *Angew. Chem. Int. Ed.* vol. 39, No. 9, pp. 1650-1652, 2000.

(Continued)

*Primary Examiner*—Kamal A Saeed
*Assistant Examiner*—Kristin Bianchi
(74) *Attorney, Agent, or Firm*—Greenblum & Bernstein, P.L.C.

(57) ABSTRACT

A method for efficiently producing L-2-amino-4-(hydroxymethylphosphinyl)-butanoic acid, useful as a herbicide, by a catalytic asymmetric synthesis reaction with a high asymmetric yield. The method includes a step in which a compound represented by the below formula (1) and a benzylamine are reacted in the presence of dehydrating agent, then the resulting mass is reacted with hydrogen cyanide in the presence of an asymmetric catalyst, followed by acid hydrolysis, further followed by elimination of a protective group. [chemical formula 1] (1) (where, $R^1$ represents a $C_{1-4}$ alkyl group).

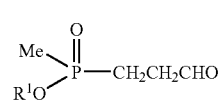

(1)

11 Claims, No Drawings

OTHER PUBLICATIONS

Mani Iyer et al., "Asymmetric Catalysis of the Strecker Amino Acid Synthesis by a Cyclic Dipeptide" *J. Am. Chem. Soc.* vol. 118, pp. 4910-4911, 1996.

Hans-Joachim Zeiss, "An Efficient Asymmetric Synthesis of Both Enantiomers of Phosphinothricin" *Tetrahedron Letters* vol. 28, No. 12, pp. 1255-1258, 1987.

Hans-Joachim Zeiss, "Enantioselective Synthesis of L-Phosphinothricin from L-Methionine and L-Glutamic Acid via L-Vinylglycine" *Tetrahedron* vol. 48, No. 38, pp. 8263-8270, 1992.

Hans-Joachim Zeiss, "Enantioselective Synthesis of Both Enantiomers of Phosphinothricin via Asymmetric Hydrogenation of α-Acylamido Acrylates" *J. Org. Chem.* vol. 56, pp. 1783-1788, 1991.

Harald Gröger, "Catalytic Enantioselective Strecker Reactions and Analogous Syntheses" *Chem. Rev.* vol. 103, pp. 2795-2827, 2003.

Petr Vachal et al., "Structure-Based Analysis and Optimization of a Highly Enantioselective Catalyst for the Strecker Reaction" *J. Am. Chem. Soc.* vol. 124, pp. 10012-10014, 2002.

METHOD FOR PRODUCING α-AMINO ACID INCLUDING PHOSPHORUS AND PRODUCTION INTERMEDIATES THEREOF

RELATED APPLICATION

The present application is an application claiming priority based on Japanese patent application no. 2006-254102, filed on Sep. 20, 2006, and the entire disclosure of said Japanese patent application is incorporated herein by reference.

FIELD OF THE INVENTION

The present invention relates to a method for producing L-2-amino-4-(hydroxymethylphosphinyl)-butanoic acid (in the below, it is abbreviated as L-AMPB) which is useful as a herbicide, and production intermediates thereof.

BACKGROUND ART

D,L-2-amino-4-(hydroxymethylphosphinyl)-butanoic acid (in the below, it is abbreviated as DL-AMPB) is a known compound having herbicidal activity, and used as an efficient herbicide having a wide range spectrum (see patent document 1).

However, the herbicidal activity of the DL-AMPB is about a half of that of L-2-amino-4-(hydroxymethylphosphinyl)-butanoic acid (in the below, it is abbreviated as L-AMPB), and it has been confirmed that its activity is due to L-AMPB itself (see patent documents 2 and 3). Therefore, it is highly desirable to develop a method for producing L-AMPB selectively and efficiently.

Conventionally, a method by utilizing microorganisms and enzymes (a), an asymmetric synthesis method (b) and the like are known as a method for producing L-AMPB. For example, a method for producing L-AMPB from 4-(hydroxymethylphosphinyl)-2-oxobutanoic acid by trans aminate enzyme (patent document 4), a method for producing L-AMPB from N-acetyl-DL-AMPB by enzymatic racemic division (patent document 5) and the like are disclosed as the method of (a). However, there are problems such that any of these methods need to be reacted with low concentration of basic material, a post-treatment and a purification process are complicated, further, expensive optically active amino acid must be used with more than the same mole ratio in a trans aminate reaction, and the like. For example, a method for producing L-AMPB from (R)-3-isopropyl-2,5-dialkoxy-3,6-dihydropyrazine by alkylation (patent document 6, non-patent document 1), a method for stereospecifically transforming L-vinylglycine into L-AMPB (non-patent document 2) and the like are disclosed as the asymmetric synthesis method of (b). However expensive optically active amino acid, such as like D-valine, L-vinylglycine and the like must be used as starting raw materials in these methods, and there is a problem in regard of supplying raw materials in large quantities at low cost. In addition, for example, a method for producing L-AMPB by asymmetric hydrogenation of 2-acetamide-4-(hydroxymethylphosphinyl)-butanoic acid (patent document 7, non-patent document 3) is disclosed as the asymmetric synthesis method. In this method, the asymmetric hydrogenation is performed using a rhodium catalyst, for which optically active diphenylphosphine compound is a ligand. However, there is a problem that expensive rhodium metal is used.

A synthesis of DL-AMPB by Strecker reaction has been already reported (patent document 8). However, there is no report that L-AMPB has been obtained selectively by an asymmetric Strecker reaction. On the other hand, the asymmetric Strecker reaction, in which optically active amino acid is synthesized from aldehyde, has been well known (non-patent document 4, non-patent document 5). However, cases where the high selectivity is obtained are limited to a case using arylaldehyde as a basic material, there are few examples that high selectivity is obtained in reactions to form an aliphatic aldehyde with straight chain. Moreover, there is almost no example in the asymmetric Strecker reaction to form aliphatic aldehyde with straight chain having substituted group with polarity like phosphate, also almost no example has been reported that the high selectivity is obtained.

Patent document 1: JP Kokai Publication 52-139727
Patent document 2: JP Kokai Publication 55-000025
Patent document 3: JP Kokai Publication 59-219297
Patent document 4: JP Kohyo Publication 2003-528572
Patent document 5: JP Kohyo Publication 2003-505031
Patent document 6: JP Kokai Publication 62-132891
Patent document 7: JP Kokai Publication 62-226993
Patent document 8: WO99/09039
Non-Patent document 1: Tetrahedron Lett. 1255 (1987)
Non-Patent document 2: Tetrahedron 8263 (1992)
Non-Patent document 3: J. Org. Chem. 56, 1783 (1991)
Non-Patent document 4: Chem. Rev., 103, 2795-2827 (2003)
Non-Patent document 5: J. Am. Chem. Soc., 124, 10012-10014 (2002)

DISCLOSURE OF THE INVENTION

Problems to be Solved by the Invention

It is an object of the present invention to provide a method for producing L-AMPB, which is useful as a herbicide, by catalytically asymmetric synthesis reaction efficiently with a high asymmetric ratio (enantiomeric excess).

Means to Solve the Problem

As a result of considering an asymmetric catalyst for the asymmetric Strecker reaction of aldehyde, the present inventors found that precursors of the L-AMPB can be provided with efficient and high enantiomeric excess when using guanidine derivative, urea derivative, zirconium derivative, aluminum derivative, titanium derivative, or lanthanoid derivative, especially using urea derivative as a catalyst, thereby the present invention has been accomplished.

That is to say, the present invention is as follows. As novel intermediates used in the method for producing L-AMPB, in a first aspect of the present invention, there is provided a compound represented by the following formula (3)

[Chemical Formula 1]

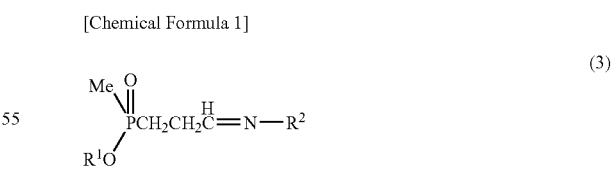

[In the formula, $R^1$ represents $C_{1-4}$ alkyl group, allyl group, $C_{1-4}$ alkyloxy $C_{1-4}$ alkyl group, $C_{1-4}$ alkyloxy $C_{1-4}$ alkyloxy $C_{1-4}$ alkyl group, aryl group, substituted aryl group, arylmethyl group, substituted arylmethyl group, tri $C_{1-4}$ alkylsilyl group or diphenylmethylsilyl group, $R^2$ represents allyl group, aryl group, substituted aryl group, arylmethyl group or substituted arylmethyl group]. Also, in a second aspect of the present invention, there is provided a compound represented by the following formula (4)

[Chemical Formula 2]

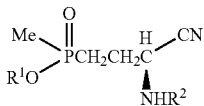
(4)

[In the formula, $R^1$ represents $C_{1-4}$ alkyl group, allyl group, $C_{1-4}$ alkyloxy $C_{1-4}$ alkyl group, $C_{1-4}$ alkyloxy $C_{1-4}$ alkyloxy $C_{1-4}$ alkyl group, aryl group, substituted aryl group, arylmethyl group, substituted arylmethyl group, tri alkylsilyl group or diphenylmethylsilyl group, $R^2$ represents allyl group, aryl group, substituted aryl group, arylmethyl group or substituted arylmethyl group].

And, in a third aspect of the present invention, there is provided a method for producing a compound represented by formula (4) set forth below, wherein a compound represented by the following formula (3)

[Chemical Formula 3]

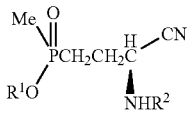
(3)

[In the formula, $R^1$ represents $C_{1-4}$ alkyl group, allyl group, $C_{1-4}$ alkyloxy $C_{1-4}$ alkyl group, $C_{1-4}$ alkyloxy $C_{1-4}$ alkyloxy $C_{1-4}$ alkyl group, aryl group, substituted aryl group, arylmethyl group, substituted arylmethyl group, tri $C_{1-4}$ alkylsilyl group or diphenylmethylsilyl group, $R^2$ represents allyl group, aryl group, substituted aryl group, arylmethyl group or substituted arylmethyl group] is reacted with hydrogen cyanide under the presence of an asymmetric catalyst:

[Chemical Formula 4]

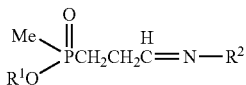
(4)

[In the formula, $R^1$ and $R^2$ represent the same meaning as above].

Also, in a forth aspect of the present invention, there is provided a method for producing a compound represented by the following formula (3)

[Chemical Formula 7]

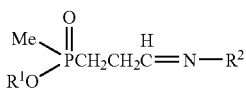
(3)

[In the formula, $R^1$ and $R^2$ represent the same meaning in the above], wherein a compound represented by the following formula (1)

[Chemical Formula 5]

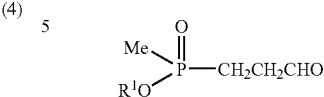
(1)

[In the formula, $R^1$ represents $C_{1-4}$ alkyl group, allyl group, $C_{1-4}$ alkyloxy $C_{1-4}$ alkyl group, $C_{1-4}$ alkyloxy $C_{1-4}$ alkyloxy $C_{1-4}$ alkyl group, aryl group, substituted aryl group, arylmethyl group, substituted arylmethyl group, tri $C_{1-4}$ alkylsilyl group or diphenylmethylsilyl group] and a compound represented by the following formula (2)

[Chemical Formula 6]

$R^2-NH_2$ (2)

[In the formula, $R^2$ represents allyl group, aryl group, substituted aryl group, arylmethyl group or substituted arylmethyl group] are reacted under the presence of a dehydrating agent.

Further, in a fifth aspect of the present invention, there is provided a method for producing L-AMPB represented by the following formula (5)

[Chemical Formula 8]

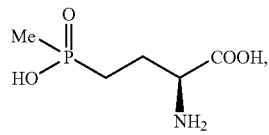
(5)

the method comprising following processes:

a process, in which a compound represented by the following formula (1)

[Chemical Formula 9]

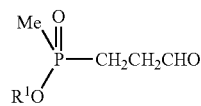
(1)

[In the formula, $R^1$ represents $C_{1-4}$ alkyl group, allyl group, $C_{1-4}$ alkyloxy $C_{1-4}$ alkyl group, $C_{1-4}$ alkyloxy $C_{1-4}$ alkyloxy $C_{1-4}$ alkyl group, aryl group, substituted aryl group, arylmethyl group, substituted arylmethyl group, tri $C_{1-4}$ alkylsilyl group or diphenylmethylsilyl group] and a compound represented by the following formula (2)

[Chemical Formula 10]

$R^2-NH_2$ (2)

[In the formula, $R^2$ represents allyl group, aryl group, substituted aryl group, arylmethyl group or substituted arylmethyl group] are reacted under the presence of a dehydrating agent to obtain a compound represented by the following formula (3)

[Chemical Formula 11]

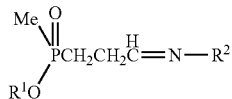
(3)

[In the formula, $R^1$ and $R^2$ represent the same meaning in the above];

a process, in which a compound represented by formula (3) is reacted with hydrogen cyanide under the presence of an asymmetric catalyst to obtain a compound represented by the following formula (4)

[Chemical Formula 12]

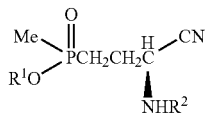
(4)

[In the formula, $R^1$ and $R^2$ represent the same meaning in the above]; and a process, in which nitrile group in the compound of formula (4) is subjected to acid hydrolysis, and further hydroxyl group and amino group moieties in the compound of formula (4) are deprotected.

EFFECT OF THE INVENTION

L-AMPB, which is useful as the herbicide, can be produced with high enantiomeric excess due to the intermediates of the present invention and the producing method thereof. The producing method of the present invention is superior to the conventional method for producing optically active substance as a low-cost, high-efficient and high selective synthesis method.

PREFERRED MODES FOR CARRYING OUT THE INVENTION

For chemical formulae in this Description, Me means methyl group, Et means ethyl group, nPr means n-propyl group, iPr means isopropyl, Ph means phenyl group, nBu means n-butyl group, secBu means sec-butyl group, and tBu means t-butyl group.

Groups shown by $R^1$, $R^2$, $R^4$, $R^5$ and $R^6$ for formulae (1) to (4) and formula (6) are explained.

Groups represented by $R^1$, $R^2$, $R^4$, $R^5$ and $R^6$ or $C_{1-4}$ alkyl groups on those groups represented by $R^1$, $R^2$, $R^4$, $R^5$ and $R^6$ mean straight chain or branched alkyl group having 1-4 carbons, in more detail, methyl group, ethyl group, n-propyl group, isopropyl group, n-butyl group, 2-butyl group, isobutyl group, t-butyl group and the like are listed.

Groups represented by $R^1$ and $R^2$ or aryl group on the groups represented by $R^1$ and $R^2$ include phenyl group or naphthyl group and the like.

Arylmethyl group represented by $R^1$ and $R^2$ means methyl group which is substituted by 1 to 3 aryl groups, in more detail, benzyl group, diphenylmethyl group, fluorenyl group and triphenylmethyl group and the like are listed.

Group represented by $R^1$ and $R^2$ or substituted aryl group on the group represented by $R^1$ and $R^2$ means that one or more hydrogen atom on benzene ring is substituted, preferably 1 to 3 hydrogen atoms are substituted; as concrete substituted group, straight chain or branched $C_{1-4}$ alkyl group such as methyl group, ethyl group, n-propyl group, isopropyl group, n-butyl group, 2-butyl group, isobutyl group, t-butyl group and the like; halogen atom such as fluorine group, chromium group, bromine group and the like; and $C_{1-4}$ alkoxy group such as methoxy group and the like; are listed. If $R^2$ represents substituted aryl group, it is preferred that its substituted group is one or more methoxy group.

Tri $C_{1-4}$ alkylsilyl group which represents $R^1$ means silyl group which is substituted with three same or different $C_{1-4}$ alkyl, in detail, tri methyl silyl group, tri ethyl silyl group, t-butyldimethylsilyl group and the like are listed.

Preferably, $C_{1-4}$ alkyloxy $C_{1-4}$ alkyl group represented by $R^1$ is methoxymethyl group.

Preferably, $C_{1-4}$ alkyloxy $C_{1-4}$ alkyloxy $C_{1-4}$ alkyl group represented by R1 is methoxyethoxymethyl group.

Preferably, $R^1$ is $C_{1-4}$ alkyl group, and more preferably methyl group.

Preferably, $R^2$ is benzyl group or p-methylbenzyl group.

For the compound of formula (1), preferably, $R^1$ is $C_{1-4}$ alkyl group, and more preferably methyl group.

Concrete examples of the compounds represented by formula (1) include 3-(methoxymethylphosphinyl)-propanal, 3-(ethoxymethylphosphinyl)-propanal, 3-(n-propyloxymethylphosphinyl)-propanal, 3-(allyloxymethylphosphinyl)-propanal, 3-(n-butyloxymethylphosphinyl)-propanal, 3-(trimethylsilyloxymethylphosphinyl)-propanal, 3-(phenoxymethylphosphinyl)-propanal, and 3-(benzyloxymethylphosphinyl)-propanal.

Preferable example is 3-(methoxymethylphosphinyl)-propanal.

The compound of formula (1) can be synthesized by the method described in Pol. J. Chem., 53, 937 (1979) or Roczniki ChemiiAnn. Soc. Chim. Polonorum, 49, 2127 (1975). (Disclosures of these documents are incorporated herein by reference.)

Concrete examples of the compounds represented by formula (2) include triphenylmethylamine, diphenylmethylamine, fluorenylamine, benzylamine, p-chlorbenzylamine, 2,4-dichlorbenzylamine, p-methoxybenzylamine, 2,4-dimethoxybenzylamine, p-methylbenzylamine, p-fluorobenzylamine, p-methoxyaniline, o-methoxyaniline, allylamine. Preferable examples are benzylamine and p-methylbenzylamine.

For the compound of formula (3), $R^1$ is preferably $C_{1-4}$ alkyl group, and more preferably methyl group. $R^2$ is preferably benzyl group or p-methylbenzyl group.

Concrete examples of the compounds represented by formula (3) include the following compounds, and compounds in which $R^1$ is methyl group and $R^2$ is benzyl group are preferable.

[Chemical Formula 13]
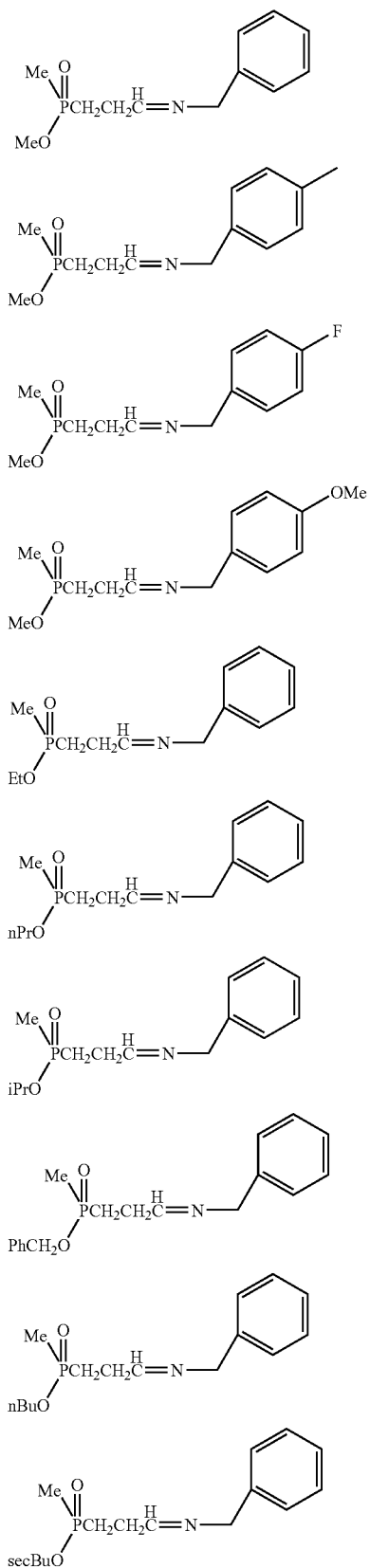
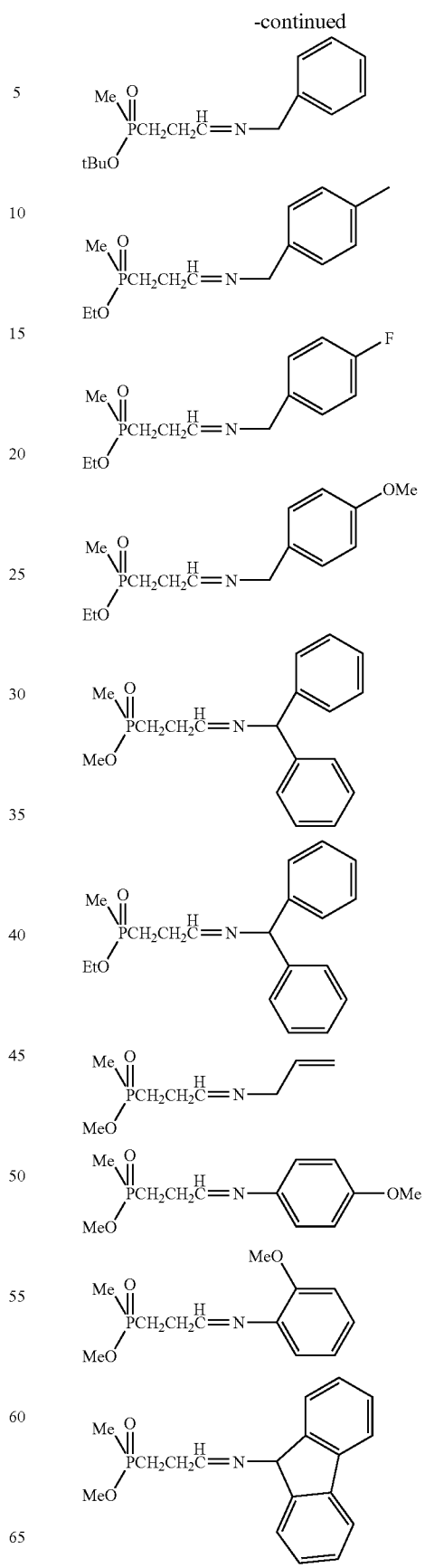

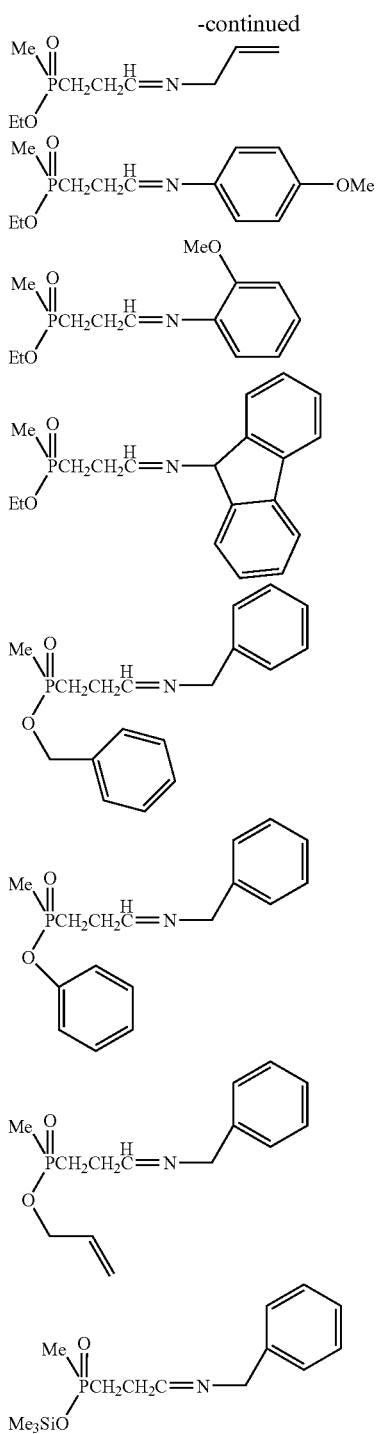

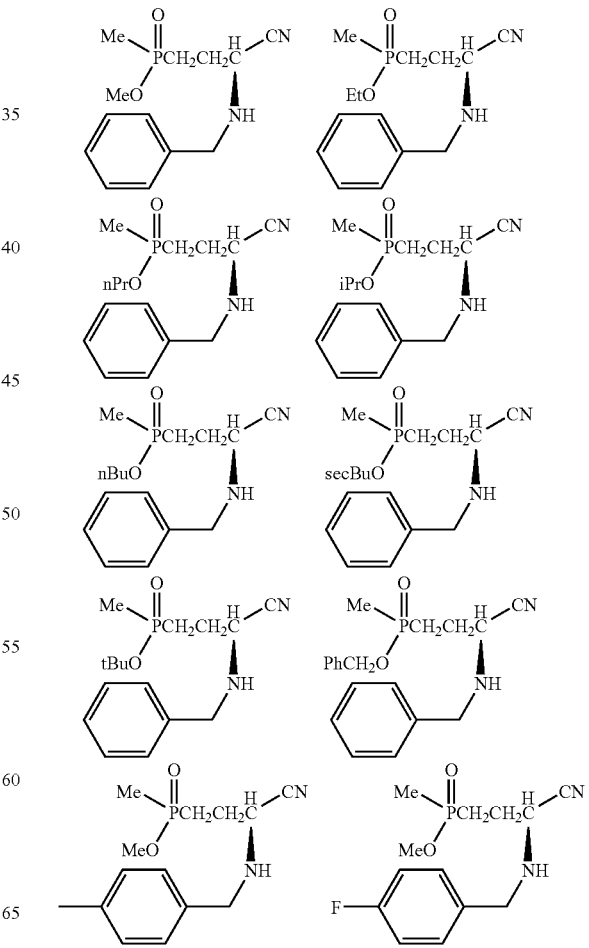

methanol. As for the dehydrating agent used herein, magnesium sulfate, sodium sulfate, molecular sieves and the like are listed, preferable is sodium sulfate. The amount of the dehydrating agent is used at 1-3 equivalent based on the amount of the compound of formula (1). Based on the used amount of the compound of formula (1), preferably, the amount of the compound represented by formula (2) is used at an equimolar amount. Reaction temperature is from 0 to 50° C., preferably, the reaction is conducted in a range from 10 to 30° C. Reaction time is usually from 10 minutes to 2 hours, preferably, the reaction is conducted in a range from 30 minutes to 1 hour.

After the reaction is finished, the dehydrating agent can be removed through filtration, and then the filtrate can be concentrated thereby to isolate the compound of formula (3). If necessary, the compound of formula (3) can be purified with silica-gel column chromatography. Normally, after the dehydrating agent is removed, for example, by filtration, the filtrate is used in a subsequent process without isolation.

For the compound of formula (4), those compounds shown below are preferred, in which $R^1$ is preferably $C_{1-4}$ alkyl group, more preferably methyl group, and $R^2$ is preferably benzyl group or p-methylbenzyl group.

Concrete examples of the compound of formula (4) include the following compounds, and compounds, in which $R^1$ is methyl group and $R^2$ is benzyl group, are preferable.

[Chemical Formula 14]

As a solvent used in the method for producing the compound of formula (3) from the compound of formula (1), halogenated hydrocarbon solvent such as methylene chloride, chloroform and the like; aromatic hydrocarbon solvent such as benzene, toluene and the like; ether solvent such as tetrahydrofuran, dimethoxyethane, dioxane and the like; aprotic polar organic solvent such as N,N-dimethylformamide, dimethylsulfoxide and the like; or alkanol solvent having 1-4 carbons such as methanol and the like are listed, and preferable solvent are toluene, methylene chloride and -continued

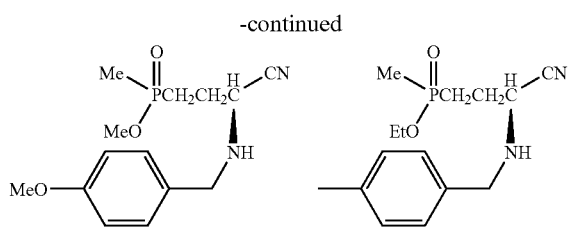

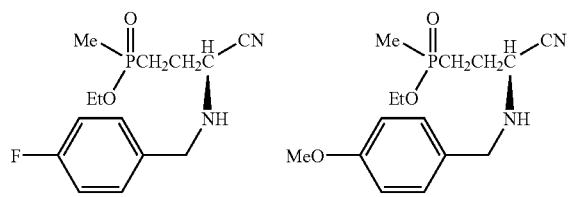

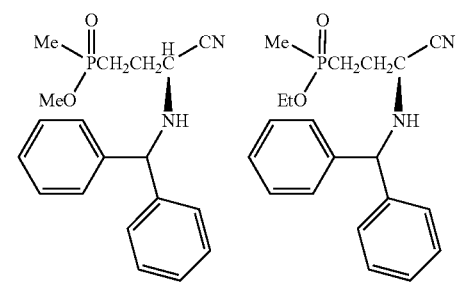

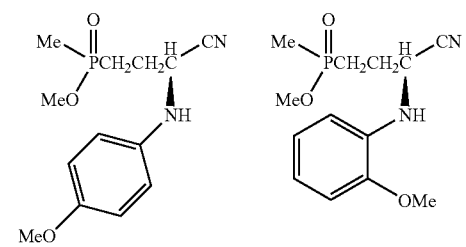

-continued

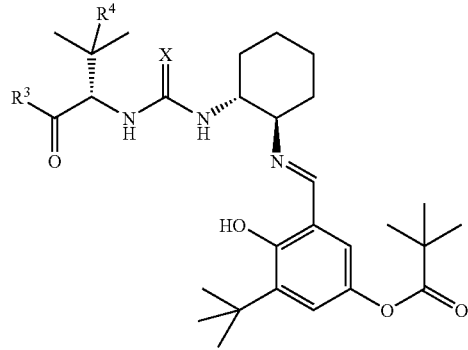

Guanidine derivatives such as those described in Org. Lett. 1, 157-160 (1999), J. Am. Chem. Soc. 118, 4910 (1996); urea derivatives such as those described in J. Am. Chem. Soc. 124, 10012-10014 (2002); zirconium derivatives c described in J. Am. Chem. Soc. 122, 762-766 (2000); aluminum derivatives such as those described in Angew. Chem. Int. Ed. 39, 1650 (2000), J. Am. Chem. Soc. 120, 5315 (1998); titanium derivatives such as those described in J. Am. Chem. Soc. 123, 11594 (2001); lanthanoid derivatives such as those described in Tetrahedron Asymmetry 12, 1147 (2001) are listed as the asymmetric catalyst used in the method for producing the compound of formula (4) from the compound of formula (3). (Disclosures of these documents are incorporated herein by reference.) There is a preferable exemplary embodiment in which the asymmetric catalyst is the urea derivative, and more preferably, a method is given in which the asymmetric catalyst is a compound represented by the following formula (6)

[Chemical Formula 15]

(6)

[In the formula, $R^3$ represents $R^5R^6N$ (herein, $R^5$ and $R^6$ are the same or different, and represent hydrogen atom, $C_{1-4}$ alkyl group, phenyl group or benzyl group respectively, except for the case where both of them are hydrogen atom at the same time), $R^4$ represents hydrogen atom or $C_{1-4}$ alkyl group, and X represents oxygen atom or sulfur atom].

In formula (6), $R^3$ is preferably $C_{1-4}$ alkylamino group, N,N-di$C_{1-4}$ alkylamino group, N-benzyl-N-$C_{1-4}$ alkylamino group, N,N-dibenzylamino group, and specifically, methylamino group, N,N-dimethylamino group, ethylamino group, N,N-diethylamino group, n-butylamino group, N,N-di n-butylamino group, benzylamino group, N-benzyl-N-methylamino group, N-benzyl-N-ethylamino group, N-benzyl-N-butylamino group, N,N-dibenzylamino group are listed, and more preferable are N,N-dimethylamino group, N,N-diethylamino group, N-benzyl-N-methylamino group and N,N-dibenzylamino group.

In formula (6), $R^4$ is preferably $C_{1-4}$ alkyl group, and more preferably methyl group.

In formula (6), X is preferably in either oxygen atom or sulfur atom, and more preferably, is oxygen atom.

The catalyst shown in formula (6) can be synthesized in a method described in J. Am. Chem. Soc. 124, 10012-10014 (2002) and J. Am. Chem. Soc. 120, 4901-4902 (1998). (Disclosures of these documents are incorporated herein by reference.)

It is mentioned that hydrogen cyanide used in the method for producing the compound of formula (4) from the compound of formula (3) is used in a liquid condition at a low temperature (from −78 to 0° C.), or hydrogen cyanide is used as a product which is dissolved in the same solvent that can be used as a reaction solvent. Alternatively, hydrogen cyanide may be used as a product which is generated (produced) in a reaction system using a mixture of $R^7CN$ (herein, $R^7$ represents silyl group, which is substituted with three, same or different, $C_{1-4}$ alkyl groups, such as trimethylsilyl group, triethylsilyl group, tert-butyldimethylsilyl group and the like) and $R^8OH$ (here, $R^8$ represents $C_{1-4}$ alkyl group), or a product which is generated (produced) in a reaction system using a mixture of MCN (here, M represents potassium, sodium) and acetic acid or ammonium chloride.

In the method for producing the compound of formula (4) from the compound of formula (3), it is mentioned, preferably, modes as sources of hydrogen cyanide to use hydrogen cyanide which is generated in a reaction system by mixing a mixture of $R^7CN$ ($R^7$ represents the same meaning as the above) and $R^8OH$ ($R^8$ represents the same meaning as the above) or a mixture of MCN (M represents the same meaning as the above) and acetic acid or ammonium chloride. It is mentioned, more preferably, to use hydrogen cyanide which is generated in a reaction system by mixing a mixture of trimethylsilylcyanide and isopropanol.

As for a solvent to be used in the method for producing the compound of formula (4) from the compound of formula (3), the following solvents are listed: halogenated hydrocarbon solvent such as methylene chloride, chloroform and the like; aromatic hydrocarbon solvent such as benzene, toluene and the like; ether solvent such as tetrahydrofuran, dimethoxyethane, dioxane and the like; aprotic polar organic solvent such as N,N-dimethylformamide, dimethylsulfoxide and the like; or alkanol solvent having 1-4 carbons such as methanol and the like are listed, and preferably, toluene, methylene chloride and methanol.

As for the amount of the asymmetric catalyst, it is used in a range from 2 to 1000 in molar ratio of the compound of formula (3)/the asymmetric catalyst, and preferably in a range from 5 to 200.

The reaction temperature is from −78 to 40° C., preferably, the reaction is conducted in a range from −40 to 30° C.

A dropping time in the case where hydrogen cyanide is used in a solvent state or as that dissolved in solvent takes 1 to 22 hours, preferably 4 to 12 hours. In the case where the mixture of $R^7CN$ and $R^8OH$ or the mixture of MCN and acetic acid or ammonium chloride is used, it is preferable that $R^7CN$ or MCN is added to the reaction solution first, and afterward, $R^8OH$ or acetic acid, ammonium chloride is dropped into the solution. The dropping time takes 1 to 22 hours, preferably 4 to 12 hours.

The amount of hydrogen cyanide is used as 3 equivalents based on the amount of the compound of formula (3), also in the case where the mixture of $R^7CN$ and $R^8OH$ or the mixture of MCN and acetic acid or ammonium chloride is used, it is used as 3 equivalents similarly. As for the reaction time, it takes usually 6 to 24 hours, preferably, ranges from 8 to 20 hours.

After the reaction is finished, the reaction solution is subjected to vacuum concentration, and purification is performed with silica-gel chromatography, thereby, the compound of formula (4) can be isolated. Typically, the reaction solvent is distilled away, and after crude product is obtained, it is used for a next process without isolation.

In the method for producing L-AMPB of formula (5) from the compound of formula (4), in the case where $R^1$ is $C_{1-4}$ alkyl group, allyl group, $C_{1-4}$ alkyloxy $C_{1-4}$ alkyl group, $C_{1-4}$ alkyloxy $C_{1-4}$ alkyloxy $C_{1-4}$ alkyl group, arylmethyl group, substituted arylmethyl group, tri $C_{1-4}$ alkylsilyl group or diphenylmethylsilyl group; $R^2$ is diphenylmethyl group, or triphenylmethyl group, the acid hydrolysis of nitrile group and the deprotection of phosphate group and amine group are performed at the same time, hydrochloric acid or sulfuric acid are listed as the acid which is used for the reaction, and water is listed as the solvent. Acid concentration is normally from 6 to 12 N when using hydrochloric acid, and in a range from 2 to 18 N when using sulfuric acid. The reaction temperature is in a range from 20 to 150° C., preferably, from 50 to 120° C., and the reaction time takes 2 to 12 hours, preferably, ranges from 4 to 8 hours.

In addition, in the case where $R^1$ is aryl group, substituted aryl group, benzyl group, substituted benzyl group, diphenylmethyl group and $R^2$ is triphenylmethyl group, arylmethyl group except fluorenyl group, substituted arylmethyl group, alkanol solvent having 1-4 carbons such as methanol, ethanol, n-propanol, isopropanol and the like, ether solvent such as dioxane, formic acid, acetic acid, hydrochloric acid, water and any combination of 2 or more solvents aforementioned are listed as solvents for deprotection, and preferably, methanol, ethanol, hydrochloric acid, water and any combination of 2 or more solvents aforementioned are listed. It is mentioned that the deprotection is performed by catalytic hydrogen reduction using catalysts such as palladium-carbon, palladium black, palladium hydroxide, platinum oxide and the like under hydrogen atmosphere. It is mentioned that the amount of catalyst for the catalytic hydrogen reduction is used at 1 to 50 weight % based on that of raw material, and preferably, 5 to 30 weight %. The reaction temperature is from 0 to 40° C., preferably from 10 to 30° C. The reaction time is from 2 to 15 hours, preferably from 4 to 12 hours.

Alternatively, in the case where $R^1$ and $R^2$ are arylmethyl group or substituted arylmethyl group, a deprotection can be also performed by Birch reduction. Liquid ammonia, ethylamine and the like are listed as the solvent. Sodium, lithium and the like are listed as the metal. A combination of liquid ammonium and metallic sodium is preferable. It is mentioned that the metal is used at 5 to 30 equivalents to raw material.

The reaction temperature is from −78 to −20° C., preferably from −40 to −30° C. The reaction time takes 2 to 15 hours, preferably 4 to 12 hours.

Moreover, in the case where $R^2$ is fluorenyl group, methoxyphenyl group, methanol, ethanol, isopropylalcohol, tetrahydrofuran, dioxane, acetonitrile, water and any combination of 2 or more thereof are listed as the solvent for the deprotection. Preferably, methanol, ethanol, tetrahydrofuran, acetonitrile, water and any combination of 2 or more thereof are listed. $Ce(NH_4)_2(NO_3)_6$ or dichlorodicyanobenzoquinone are listed as a reactant for the deprotection. It is mentioned that the used amount of the reactant is 1 to 6 equivalents based on the raw material, preferably 2 to 5 equivalents. The reaction temperature is from −20 to 40° C., preferably from 0 to 20° C. The reaction time takes 2 to 15 hours, preferably 4 to 12 hours.

Further, in the case where $R^2$ is allyl group, methanol, ethanol, acetonitrile, tetrahydrofuran, dichloromethane and the like are listed as the solvent for the deprotection. $(Ph_3P)_3RhCl$, $Pd(PhP)_4$ are listed as a reactant. $Pd(PhP)_4$ is preferable. It is mentioned that the used amount of the reactant is 0.01 to 0.2 equivalents based on the raw material, preferably 0.05 to 0.1 equivalents. The reaction temperature is from −20 to 70° C., preferably from 0 to 40° C. The reaction time takes 1 to 15 hours, preferably 2 to 12 hours.

For example, the compound of formula (5) can be isolated-purified using ionic exchange resin (Dowex 1X2 Ac, 200-400 mesh: eluent 10% acetic acid solution) by following the ordinary method.

According to an other preferred mode, there is provided a method for producing compounds of formula (4) from compounds of formula (3), including the manufacturing process of the compound of formula (3) by reacting the compound represented by formula (1) with the compound represented by formula (2).

According to a further other preferred mode, there is provided a method for producing the compound of formula (4) from the compound of formula (3), to obtain L-2-amino-4-(hydroxymethylphosphinyl)-butanoic acid represented by formula (5) the method including a process of subjecting nitrile group in the compound of formula (4) to acid hydrolysis, and further protecting hydroxyl group and amino group moieties of the compound of formula (4).

EXAMPLES

The present invention is further described with reference to the following examples, which are not intended to restrict the present invention.

Measurement of an Enantiomeric Excess

The enantiomeric excess (asymmetric yield ratio) was measured using High-Performance Liquid Chromatography (HPLC) with a compound of formula (5) manufactured in the following conditions. D-form is eluted firstly, then L-form is eluted.
Column: SUMICHIRAI. OA6100 (4.6×150 mm)
Mobile Phase: 2 mM Copper sulfate aqueous solution
Detection: UV254 nm
Flow Rate: 1.0 ml/min
Column Temperature: 30° C.

Example 1

Manufacturing of
L-2-amino-4-(hydroxymethylphosphinyl)-butanoic acid

Sodium sulfate anhydride (280 mg) was added to a solution obtained by dissolving 3-(methoxymethylphosphinyl)-propanal (600 mg) and benzylamine (428 mg) in toluene (10 ml), then the solution was stirred for an hour at ambient temperature. Sodium sulfate was filtered out, then the filtrate thus obtained was added to a solution prepared in other reaction container at ambient temperature, which solution contains an asymmetric catalyst (compound represented by formula (6), where $R^3$: dimethylamine, $R^4$: methyl, X: oxygen atom) (336 mg) and toluene (1 ml). This solution was cooled at −40° C., then trimethylsilylcyanide (1.19 g) was added to this solution. Further, a solution of isopropanol (722 mg) and toluene (6 ml) was dropped at −40° C. over 7 hours. After dropping, the solution was stirred for 15 hours at the same temperature. After hydrogen cyanide was distilled away under the reduced pressure, the solution was raised up to ambient temperature and solvent was distilled away under the reduced pressure to obtain a residue 1. Concentrated hydrochloric acid (10 ml) was added to the residue 1, and the resultant mixture was heated to reflux for 6 hours. After cooling down to room temperature, the solvent was distilled away under the reduced pressure. Water (10 ml) and 10% Pd/C (50 mg) were added to the residue, and the resultant mixture was stirred at room temperature for 27 hours under a hydrogen atmosphere. Pd/C was filtered out and the resultant filtrate was concentrated under reduced pressure, then propyleneoxide (10 ml) was added to the obtained residue. The mixture obtained was stirred for an hour. After vacuum concentration, the obtained residue was purified with ionic exchange resin (Dowex 1X2 Ac, 200-400 mesh: eluent 10% acetic acid solution) to obtain objective L-2-amino-4-(hydroxymethylphosphinyl)-butanoic acid as solid (405 mg).

HPLC analysis (retention time: D form 6.8 min., L form: 8.6 min.) showed L:D=91:9

$^1$H-NMR ($D_2O$) δ: 1.28 (3H, d, J=13.9 Hz), 1.57-1.78 (2H, m), 1.95-2.11 (2H, m), 3.89 (1H, t, J=6.1 Hz).

APIMASS: m/z 182 $[M+H]^+$.

Example 2

Manufacturing of
L-2-amino-4-(hydroxymethylphosphinyl)-butanoic acid

Instead of the asymmetric catalyst in Example 1, a compound of formula (6) ($R^3$=diethylamine, $R^4$=methyl, X=oxygen atom) was used as an asymmetric catalyst and a reaction was performed in the same manner as in Example 1. Thereby, objective L-2-amino-4-(hydroxymethylphosphinyl)-butanoic acid (358 mg) was obtained from 3-(methoxymethylphosphinyl)-propanal (480 mg). According to HPLC analysis, L:D=86:14 was shown.

Example 3

Manufacturing of
L-2-amino-4-(hydroxymethylphosphinyl)-butanoic acid

Instead of benzylamine in Example 1, p-methylbenzylamine was used and a reaction was performed in the same manner as in Example 1. Thereby, objective L-2-amino-4-(hydroxymethylphosphinyl)-butanoic acid (232 mg) was obtained from 3-(methoxymethylphosphinyl)-propanal (600 mg). According to HPLC analysis, L:D=87:13 was shown.

Example 4

Manufacturing of L-2-amino-4-(hydroxymethylphosphinyl)-butanoic acid

Instead of the asymmetric catalyst in Example 1, a compound of formula (6) ($R^3$=dibenzylamine, $R^4$=methyl, X=oxygen atom) was used as an asymmetric catalyst and a reaction was performed in the same manner as in Example 1. Thereby, objective L-2-amino-4-(hydroxymethylphosphinyl)-butanoic acid (210 mg) was obtained from 3-(methoxymethylphosphinyl)-propanal (450 mg). According to HPLC analysis, L:D=87:13 was shown.

Example 5

Manufacturing of L-2-amino-4-(hydroxymethylphosphinyl)-butanoic acid

Instead of benzylamine in Example 1, diphenylmethylamine was used and a reaction was performed in the same manner as in Example 1. Thereby, objective L-2-amino-4-(hydroxymethylphosphinyl)-butanoic acid (696 mg) was obtained from 3-(methoxymethylphosphinyl)-propanal (900 mg). According to HPLC analysis, L:D=61:39 was shown.

Example 6

Manufacturing of L-2-amino-4-(hydroxymethylphosphinyl)-butanoic acid

Instead of the asymmetric catalyst in Example 1, a compound of formula (6) ($R^3$=dimethylamine, $R^4$=methyl, X=sulfur atom) was used as an asymmetric catalyst and a reaction was performed in the same manner as in Example 1. Thereby, objective L-2-amino-4-(hydroxymethylphosphinyl)-butanoic acid (185 mg) was obtained from 3-(methoxymethylphosphinyl)-propanal (450 mg). According to HPLC analysis, L:D=94:6 was shown.

Example 7

Manufacturing of L-2-amino-4-(hydroxymethylphosphinyl)-butanoic acid

Instead of the asymmetric catalyst in Example 1, a compound of formula (6) ($R^3$=dimethylamine, $R^4$=hydrogen atom, X=oxygen atom) was used as an asymmetric catalyst and a reaction was performed in the same manner as in Example 1. Thereby, objective L-2-amino-4-(hydroxymethylphosphinyl)-butanoic acid (525 mg) was obtained from 3-(methoxymethylphosphinyl)-propanal (750 mg) According to HPLC analysis, L:D=87:13 was shown.

Example 8

N-benzyl-3-(methoxymethylphosphinyl)-propylideneamine

Sodium sulfate anhydride (120 mg) was added to a solution obtained by dissolving 3-(methoxymethylphosphinyl)-propanal (60 mg) and benzylamine (42.8 mg) in toluene (3 ml), then the resultant solution was stirred for an hour at room temperature. Sodium sulfate was filtered out, and the resultant filtrate was concentrated to obtain N-benzyl-3-(methoxymethylphosphinyl)-propylideneamine (87 mg).

$^1$H-NMR (CDCl$_3$) δ: 1.46 (3H, d, J=13.7 Hz), 2.07 (2H, dt, J=13.7, 8.1 Hz), 2.57-2.67 (2H, m), 3.69 (3H, d, J=10.7 Hz), 4.60 (2H, s), 7.22-7.38 (5H, m), 7.89 (1H, t, J=3.7 Hz)

FABMASS: m/z 240[M+H]$^+$.

Example 9

L-2-benzylamino-4-(methoxymethylphosphinyl)-propionitrile

A residue 1 obtained from 3-(methoxymethylphosphinyl)-propanal (72 mg) by conducting the same reaction as in Example 1 was purified with Preparative TLC (chloroform:methanol=12:1) to obtain L-2-benzylamino-4-(methoxymethylphosphinyl)-propionitrile (59 mg).

$^1$H-NMR (D$_2$O) 67 : 1.48 (3H, d, J=13.7 Hz), 1.85-2.00 (2H, m), 2.03-2.13 (2H, m), 3.60 (1H, dd, J=14.8, 7.0 Hz), 3.70 (3H, dd, J=11.0, 1.2 Hz), 3.84 (1H, d, J=12.9 Hz), 4.08 (1H, d, J=12.9 Hz), 7.28-7.37 (5H, m)

FABMASS: m/z 267 [M+H]$^+$

From aforementioned Examples, it has been achieved that L versus D (L:D) yield, in which L is at least 61%, further L is not less than 86 to 87% or 91% or above, a maximum at L 94%.

INDUSTRIAL APPLICABILITY

The present invention resides in that guanidine derivative, urea derivative, zirconium derivative, aluminum derivative, titanium derivative and lanthanoid derivative are used as a catalyst, and the compound represented by formula (3) is subjected to an asymmetric strecker reaction to produce L-AMPB selectively. The present invention is superior to the conventional method for producing optically active substance, in regard of producing at low-cost, efficiently and high-selectively. Therefore, the present invention is extremely useful industrially, especially for the field of pharmaceuticals needed for herbicidal action.

It should be also understood that the foregoing disclosure based on examples however the present invention is not limited to aforementioned examples. Further, changes and modifications are possible based on the essential technical concept within the entire disclosure of the invention (including claims). Various combinations, substitutions or selections of various disclosed constitutional elements or features may be made within the claims. Patent and non-patent documents which are referred or quoted in the present Description are incorporated in the present Description by reference thereto.

The invention claimed is:

1. A method for producing a compound represented by the following formula (4), wherein a compound represented by the following formula (3) is reacted with hydrogen cyanide under the presence of an asymmetric catalyst:

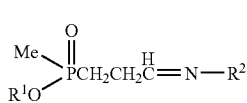

(3)

[In the formula, $R^1$ represents $C_{1-4}$ alkyl group, allyl group, $C_{1-4}$ alkyloxy $C_{1-4}$ alkyl group, $C_{1-4}$ alkyloxy $C_{1-4}$ alkyloxy $C_{1-4}$ alkyl group, aryl group, substituted aryl group, arylmethyl group, substituted arylmethyl group, tri $C_{1-4}$ alkylsilyl group or diphenylmethylsilyl group; $R^2$ represents allyl group, aryl group, substituted aryl group, arylmethyl group or substituted arylmethyl group];

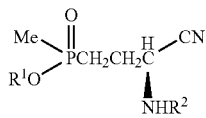

(4)

[In the formula, $R^1$ and $R^2$ represent the same meaning as aforementioned].

2. A method for producing a compound represented by the following formula (3), wherein a compound represented by the following formula (1) and a compound represented by the following formula (2) are reacted under the presence of dehydrating agent:

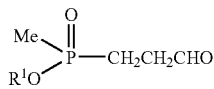

(1)

[In the formula, $R^1$ represents $C_{1-4}$ alkyl group, allyl group, $C_{1-4}$ alkyloxy $C_{1-4}$ alkyl group, $C_{1-4}$ alkyloxy $C_{1-4}$ alkyloxy $C_{1-4}$ alkyl group, aryl group, substituted aryl group, arylmethyl group, substituted arylmethyl group, tri $C_{1-4}$ alkylsilyl group or diphenylmethylsilyl group];

(2)

[In the formula, $R^2$ represents allyl group, aryl group, substituted aryl group, arylmethyl group or substituted arylmethyl group]; and

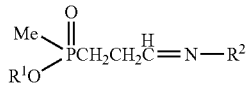

(3)

[In the formula, $R^1$ and $R^2$ represent the same meaning as aforementioned].

3. The method according to claim 1, wherein said method comprises the process of allowing the compound represented by the following formula (1) to react with a compound represented by the following formula (2) under the presence of dehydrating agent to produce the compound represented by formula (3):

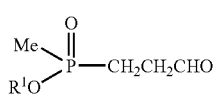

(1)

[In the formula, $R^1$ represents $C_{1-4}$ alkyl group, allyl group, $C_{1-4}$ alkyloxy $C_{1-4}$ alkyl group, $C_{1-4}$ alkyloxy $C_{1-4}$ alkyloxy $C_{1-4}$ alkyl group, aryl group, substituted aryl group, arylmethyl group, substituted arylmethyl group, tri $C_{1-4}$ alkylsilyl group or diphenylmethylsilyl group]; and

(2)

[In the formula, $R^2$ represents allyl group, aryl group, substituted aryl group, arylmethyl group or substituted arylmethyl group].

4. The method according to claim 1, wherein said method comprises a process of subjecting nitrile group in the compound of formula (4) to acid hydrolysis, and further deprotecting hydroxyl group and amino group moieties in the compound of formula (4) to obtain L-2-amino-4-(hydroxymethylphosphinyl)-butanoic acid represented by the following formula (5):

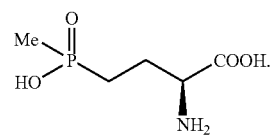

(5)

5. The method according to claim 1, wherein said $R^1$ is $C_{1-4}$ alkyl group, and $R^2$ is benzyl group or p-methylbenzyl group.

6. A method for producing L-2-amino-4-(hydroxymethylphosphinyl)-butanoic acid represented by the following formula (5);

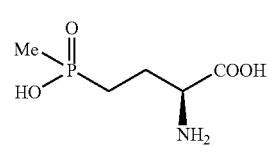

(5)

said method comprising:

a process of allowing a compound represented by the following formula (1) to react with a compound represented by the following formula (2) under the presence of dehydrating agent to obtain a compound represented by the following formula (3);

a process of allowing a compound represented by the following formula (3) to react with hydrogen cyanide under the presence of an asymmetric catalyst to obtain a compound represented by the following formula (4); and a process of allowing nitrile group in the compound of formula (4) to acid hydrolysis, and further deprotecting hydroxyl group and amino group moieties in the compound of formula (4);

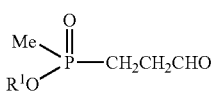

(1)

[In the formula, $R^1$ represents $C_{1-4}$ alkyl group, allyl group, $C_{1-4}$ alkyloxy $C_{1-4}$ alkyl group, $C_{1-4}$ alkyloxy $C_{1-4}$ alkyloxy $C_{1-4}$ alkyl group, aryl group, substituted aryl group, arylmethyl group, substituted arylmethyl group, tri $C_{1-4}$ alkylsilyl group or diphenylmethylsilyl group];

(2)

[In the formula, $R^2$ represents ally group, aryl group, substituted aryl group, arylmethyl group or substituted arylmethyl group];

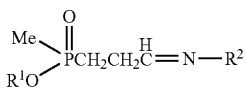

(3)

[In the formula, $R^1$ and $R^2$ represent the same meaning as aforementioned]; and

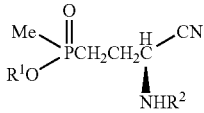

(4)

[In the formula, $R^1$ and $R^2$ represent the same meaning as aforementioned].

7. The method according to claim 1, wherein said asymmetric catalyst is a compound represented by the following formula (6):

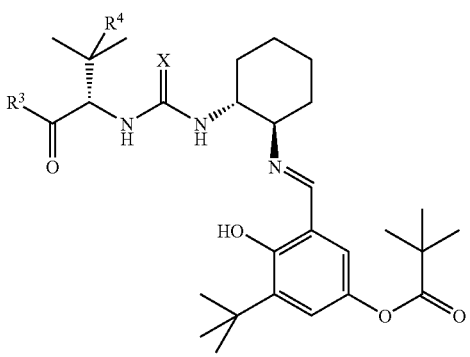

(6)

[In formula (6), $R^3$ represents $R^5R^6N$ (herein, $R^5$ and $R^6$ are the same or different, and represent hydrogen atom, $C_{1-4}$ alkyl group, phenyl group or benzyl group respectively, except for the case where both of them are hydrogen atom at the same time), $R^4$ represents hydrogen atom or $C_{1-4}$ alkyl group, X represents oxygen atom or sulfur atom].

8. The method according to claim 1, wherein said hydrogen cyanide is a product generated in a reaction system using a mixture of a compound represented by $R^7CN$ (herein, $R^7$ represents trimethylsilyl group, triethylsilyl group, or tert-butyldimethylsilyl group) and a compound represented by $R^8OH$ (herein, $R^8$ represents $C_{1-4}$ alkyl group); or a product generated in a reaction system using a mixture of a compound represented by MCN (herein, M represents potassium or sodium) and acetic acid or ammonium chloride.

9. A compound represented by the following formula (3):

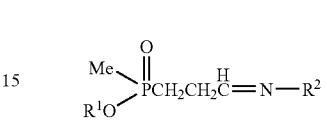

(3)

[In the formula, $R^1$ represents $C_{1-4}$ alkyl group, allyl group, $C_{1-4}$ alkyloxy $C_{1-4}$ alkyl group, $C_{1-4}$ alkyloxy $C_{1-4}$ alkyloxy $C_{1-4}$ alkyl group, aryl group, substituted aryl group, arylmethyl group, substituted arylmethyl group, tri $C_{1-4}$ alkylsilyl group or diphenylmethylsilyl group; $R^2$ represents allyl group, aryl group, substituted aryl group, arylmethyl group or substituted arylmethyl group].

10. A compound represented by the following formula (4):

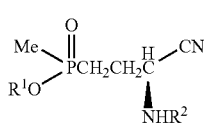

(4)

[In the formula, $R^1$ represents $C_{1-4}$ alkyl group, allyl group, $C_{1-4}$ alkyloxy $C_{1-4}$ alkyl group, $C_{1-4}$ alkyloxy $C_{1-4}$ alkyloxy $C_{1-4}$ alkyl group, aryl group, substituted aryl group, arylmethyl group, substituted arylmethyl group, tri $C_{1-4}$ alkylsilyl group or diphenylmethylsilyl group; $R^2$ represents allyl group, aryl group, substituted aryl group, arylmethyl group or substituted arylmethyl group].

11. The method according to claim 2, wherein said $R^1$ is $C_{1-4}$ alkyl group, and $R^2$ is benzyl group or p-methylbenzyl group.

* * * * *